United States Patent [19]

Neidleman et al.

[11] 4,282,324
[45] Aug. 4, 1981

[54] METHOD FOR PRODUCING IODINE

[75] Inventors: Saul L. Neidleman, Oakland; John Geigert, Concord, both of CA

[73] Assignee: Cetus Corporation, Berkeley, Calif.

[21] Appl. No.: 51,847

[22] Filed: Jun. 25, 1979

[51] Int. Cl.³ ............................................... C12P 3/00
[52] U.S. Cl. .................................. 435/168; 435/171; 435/911
[58] Field of Search ........................ 435/168, 171, 911

[56] References Cited

PUBLICATIONS

Pommier et al., *Eur. J. Biochem.*, 38(1973) 497–506.
Pommier et al., Chemical Abstracts, 80:34688x, p. 98 (1974).
Lambert et al., Chemical Abstracts, 85:43309e, 43310 (1976).
David et al., *Biochemistry*, 13(5), 1014–1021 (1974).
Davidson et al., *Biochem. et Biophys. Acta*, 522, 318–326 (1978).

*Primary Examiner*—Esther M. Kepplinger
*Attorney, Agent, or Firm*—Fitch, Even, Tabin, Flannery & Welsh

[57] ABSTRACT

This invention relates to the production of iodine. More particularly, the invention relates to the enzymatic oxidation of iodide to iodine and the recovery of said formed iodine.

8 Claims, No Drawings

METHOD FOR PRODUCING IODINE

This invention relates to the production of iodine. More particularly, the invention relates to the enzymatic oxidation of iodide to iodine and the recovery of said formed iodine.

There is an increasing demand for increased supplies of iodine and its major derivatives, iodide salts. The consumption of iodine and iodide salts is distributed among several industrially significant applications: catalysts, animal feed additions, stabilizers (as in nylon precursors), inks and colorants, pharmaceuticals, sanitary and industrial disinfectants, film, and other uses. The development of an economical process for more efficient and expanded production of iodine would be of a valuable contribution to the chemical industry.

A brief description (source: Ency. Chem. Tech., 2nd Edition, R. E. Kirk and D. F. Othmer, Wiley-Interscience, N.Y., N.Y., 1965-Vol. 7) of typical processes for the production of iodine from brines follows:

"The first step in each of these (iodine production processes from brine) is the clarification of the brine to remove oil and other suspended material. In one process, a silver nitrate solution is added to precipitate silver iodide, which is filtered and treated with scrap iron to form metallic silver and a solution of ferrous iodide. The silver is redissolved in nitric acid for use in another cycle, and the solution is treated with chlorine to liberate the iodine.

"The largest part of the U.S. production is as a by-product from Michigan natural brines. The iodine is recovered by a process resembling that for recovery of bromine from seawater. The brine, containing from 30–40 ppm iodine, is acidified with sulfuric acid and treated with a slight excess of chlorine to liberate the iodine. It is then pumped to a denuding tower in which it gives up its iodine to a counter-current stream of air. The air passes to a second tower where the iodine is absorbed by a solution of hydriodic and sulfuric acids. This solution is treated with sulfur dioxide to reduce the iodine to hydriodic acid, and part is drawn off to a reactor for recovery of iodine, while the remainder is recirculated to the absorption tower. The liquor in the reactor is treated with chlorine and the liberated iodine is settled, filtered, melted in a kettle under concentrated sulfuric acid, and cast into pigs.

"The process used by the Chilean nitrate industry differs from the others since the iodine is present as iodate. The iodine is extracted from the caliche as sodium iodate and is allowed to accumulate in the mother liquors from crystallization of sodium nitrate until a suitable concentration, about 6 g/liter, has been attained. Part is then drawn off and treated with the exact quantity of sodium bisulfite solution required to reduce all of the iodate to iodide.

$$2NaIO_3 + 6NaHSO_3 \rightarrow 2NaI + 3Na_2SO_4 + 3H_2SO_4$$

"This mixture, now acid with sulfuric acid resulting from the oxidation of the sulfur dioxide, is treated with just sufficient fresh mother liquor to liberate all the iodine in accordance with the reaction.

$$5NaI + NaIO_3 + 3H_2SO_4 \rightarrow 3I_2 + 3Na_2SO_4 + 3H_2O$$

"An additional source of iodine is seaweed from which some of the Japanese production has been derived."

It is an object of the present invention to provide an improved method for producing iodine.

Another object of the invention is to provide a process for producing iodine which does not require the expensive and dangerous substance, chlorine, common to many present processes and which is energy-intensive to produce.

Another object of the invention is to provide a method for producing iodine which may be conducted at ambient temperature and atmospheric pressure.

Another object of the invention is to provide a method for producing iodine which minimizes waste disposal problems to provide both economic and ecological benefits.

Another object of the invention is to provide an improved method for producing iodine wherein selectivity for iodine recovery, even in the presence of bromide and chloride, is provided.

A further object of the invention is to provide a method for producing iodine from relatively plentiful sources of iodide, such as brines and bitterns, rather than from less plentiful and more inconsistent sources such as seaweed and mining products.

The ability of halogenating enzymes to catalyze the oxidation of iodide is well established. For example, phenols and proteins are iodinated by these enzymes. However, in these reactions, molecular iodine is not the preferred intermediate. In fact, many have questioned whether molecular iodine is even formed (B. Davidson, J. T. Neary, et al. Biochim Biophy Acta, 522, 318 (1978)). While others have recognized the catalytic ability of these enzymes, the invention of a process to produce iodine by this method has not been previously described.

The method of the invention comprises providing a reaction mixture of pH buffered water, a halogenating enzyme, an oxidizing agent and a source of ionic iodide. The reaction is run in the absence of iodine acceptor substrates which allows the recovery of iodine from the reaction mixture.

The starting material or source of ionic iodide may be any of a variety of brines or bitterns. The process may be used economically to recover iodine from natural brines, bitterns, salt lakes, and the like.

The halogenating enzyme used in the reaction mixture may be in pure form, free or immobilized, or may be in microbial cells which produce the enzyme. Among the halogenases useful in the practice of this invention are those derived from the microorganism Caldariomyces fumago, seaweed, milk (lactoperoxidase), thyroid (thyroid peroxidase), leukocytes (myeloperoxidase) and horseradish (horseradish peroxidase). Sufficient water is employed in the reaction mixture to wet the enzyme and, in fact, may be the major solvent in the reaction mixture.

The oxidizing agent employed in the reaction mixture may be of any suitable type, preferably hydrogen peroxide. The hydrogen peroxide need not be purified, but may be used in dilute form to reduce the cost of the hydrogen peroxide with respect to concentrated purified material. In addition, the use of dilute hydrogen peroxide increases the safety of usage and extends the life of the halogenating enzyme. The hydrogen peroxide may be added directly to the mixture in a single batch addition, or may be added in a continuous slow feed. Alternatively, the hydrogen peroxide may be generated as slow feed in situ by the use of a hydrogen peroxide-producing enzyme or chemical system. Such enzyme systems are well known in the art and include glucose oxidase in the presence of glucose; glucose-2-oxidase in the presence of glucose; methanol oxidase in the presence of methnoal; D- and L-amino acid oxidases in the presence of D- and L-methionine; and diamine oxidases in the presence of histamine.

Any or all of the enzymes or cells producing the enzymes in this invention may be used in either free or immobilized form. The processes for enzyme and cell immobilization are familiar to those skilled in the art and include reacting a solution of the enzyme or cells with one of a broad range of organic and inorganic supports. Included among these are polyacrylamide, ethylenemaleic acid copolymers, methacrylic-based polymers, polypeptides, styrene-based polymers, agarose, cellulose, dextran, porous glass beads, and aluminum or titanium hydroxide. Enzymes and cells in immobilized form have increased stability, extended usefulness, and recoverability. Reactions employing immobilized enzymes and cells may be run in columns or reaction tanks.

The iodine recovery reaction of the invention is conducted within the pH range of from about 2 to about 8, which is enzyme-dependent. The pH of the reaction is maintained within the desired range by use of a buffering agent. Suitable buffers include sodium or potassium phosphate, gluconate, citrate, formate, and acetate-based systems. The reaction may be conducted in an aqueous medium.

The production of iodine results during the course of the reactions which take place in the above reaction mixture. The iodine may be recovered by any convenient means, and may be produced either continuously or by batch processing. The reaction may be run in the presence of solvents which are immiscible in water and which can selectively extract the iodine as it is formed. Such solvents should, of course, have a non-detrimental effect on the enzymes used in the process. By extracting the iodine as it is formed, the use of such solvents will reduce the iodine toxicity to the enzyme and aid in the recovery of the free iodine. Among solvents that are suitable are benzene, toluene, xylene, mesitylene, ethyl acetate, ethyl ether, carbon tetrachloride and carbon disulfide.

Another simple technique for continuous removal of iodine from the reaction is to bubble an inert gas, such as nitrogen, through the reaction mixture. The iodine is thus carried in the gas phase, is removed and concentrated from the gas stream by sublimation or other procedures known to the art. The spent inert gas is recycled for reuse.

The reaction is preferably conducted in the temperature range of 15° C. to about 50° C., preferably about 20° C. to about 30° C.

For purposes of further illustrating the invention, the following examples are set forth. These examples are not intended to limit the scope of the invention.

EXAMPLE 1

This example shows the pH range of activity for various halogenating enzymes useful in this process.

Dilute hydrogen peroxide (0.044 mmoles; 273 μg/ml final), potassium iodide (0.42 mmoles; 9730 μg/ml final) and 0.1 M potassium phosphate buffer are mixed together to a final volume of 5 milliliters in a 100 milliliter Pyrex flask at room temperature and room pressure. The halogenating enzyme is added.

The halogenating enzymes are prepared as follows:

Chloroperoxidase (CP). Mycelial pads of *Caldariomyces fumago* (ATCC 16373) are grown on potato agar slants as follows: Sliced potato (200 g) is cooked in distilled water (500 ml) for 40 minutes and then strained. A solution of glucose (21 g) and agar (20 g) in distilled water (500 ml) is added to the strained solution. The pH is adjusted to 6.8 and the volume is brought to 1 liter with distilled water. The medium is sterilized at 121° for 15 minutes. The organism is inoculated on the potato agar slants, produced in accordance with the above procedure, and is grown for about one week at room temperature. The organism is then used to inoculate the soybean-glucose medium (50 ml) prepared as follows: to 1 liter of distilled water are added extraction process soybean meal (30 g), glucose (30 g), and $CaCO_3$ (7 g). The medium is sterilized at 121° for 30 minutes and is then inoculated with the organism after cooling. The organism is grown for 4–5 days on a rotary shaker at 25°. 5 ml of this material is used to inoculate a 500 ml Erlenmeyer flask containing 100 ml of a modified Czepek-Dox medium prepared by adding the following to 1 liter of distilled water: $NaNO_3$ (3 g), $KH_2PO_4$ (1 g), KCl (0.5 g), $MgSO_4.7H_2O$ (10 mg) and glucose (40 g). The medium is sterilized at 121° for 20 minutes prior to inoculation with the organism. The organism is grown under static conditions at room temperature 5–7 days. The black mycelial pads which form are collected, rinsed with distilled water, and stored in plastic bags in a freezer at −10° for subsequent use.

The halogenating enzyme is prepared by grinding 6 mycelial pads (prepared in accordance with the above procedures) with 60 g acid-washed sand and 60 ml distilled water for 2 minutes in a Virtis 45 homogenizer. The homogenate is centrifuged while cold and the supernatant solution filtered through Whatman #1 paper at room temperature. The filtrate is concentrated about 10-fold using a rotary film evaporator at reduced pressure and temperature less than 35°. The concentrate is chilled at 0° in an ice bath, and prechilled (0°) ethanol is added until 45% ethanol (v/v) is reached. The mixture is stirred vigorously for 15 minutes, and then centrifuged at −10° (at 15,000 g) with a 55-34 rotor in a Sorval RC-5 Superspeed for 15 minutes. The black sediment is discarded. To the centrifugate, cooled at 0°, is added additional prechilled ethanol to give 65% ethanol (v/v). The mixture is slowly stirred for 30 minutes at 0°, and then centrifuged as before. The centrifugate is discarded and the precipitate containing the chloroperoxidase activity is dissolved in a minimum volume of 0.05 M potassium buffer (pH 7). The enzyme solution is stored at −20°. The activity is measured as 80 monochlorordimedon units/ml. (Ref: Morris, D. R. and Hager, L. P., *J. Biol. Chem.* 241 1763 (1966). 20 units added to the reaction.

Lactoperoxidase (LP). Purchased from Sigma Chemical Company (Catalogue #L-7129; activity of 470 purpurogallin units/ml). 200 units added to reaction.

Seaweed Peroxidase (SWP). *Coralina sp.* obtained along the coast of La Jolla, California is ground in a Virtis 45 homogenizer for 5 minutes in distilled water. The homogenate is spun at 20,000 rpm for 20 minutes. The supernatant is decanted and saved. The pellet is resuspended in distilled water and recentrifuged. This supernatant and previous supernatant are combined. The solution is brought first to 33%, then to 55% saturation in ammonium sulfate. Centrifugation and separation of pellet is performed at each step. The 33%-55% pellet fraction is passed through a DEAE column using a 0.3 M to 1 M phosphate buffer (pH 6.0) gradient. The fraction which elutes at 1 M is dialyzed against 20 mM phosphate buffer (pH 6) overnight. This preparation is stored at −20° until needed. The activity is measured as 2 monochlorodimedon units/ml. 1 unit is added to the reaction.

Horseradish Peroxidase (HRP). Purchased from Sigma Chemical Company (Catalog #P-8250; activity of 165 purpurogallin units/mg solid). 500 units added to the reaction.

The reaction mixtures are allowed to stand for 5 minutes and then 10 ml of chloroform is added to each one. The reaction mixtures are shaken and the violet coloration in the chloroform layer measured at 510 nm. Iodine standards are prepared by dissolving the appropriate amount of iodine (Baker Chemical Company, 99.9% pure) in chloroform.

Product identity was confirmed by injecting 10 μl of the reaction mixture into a Finnigan Model 4021 gas chromatograph/mass spectrometer/data system, equipped with a 6 foot by ¼ inch coiled, glass column, packed with Tenax-GC (60/80 mesh). Carrier gas (helium) flow rate was set at 25 ml/minute. The column temperature was programmed from 100° C. to 250° C. at a rate of 10° C./minute. The mass spectrometer was set on electron impact ionization mode, 70 eV. Iodine elutes from the column near 200° C. Iodine has a characteristic mass spectrum: 2 single peaks of high abundance, m/e 127 and m/e 254.

Variable conditions and results are set forth in Table I.

TABLE I

| | IODINE PRODUCED, mg** | | | | |
|---|---|---|---|---|---|
| pH | Non-enzymatic* | CP Enzymatic | LP Enzymatic | SWP Enzymatic | HRP Enzymatic |
| 2.0 | 3.5 | 4.1 | 1.5 | 2.1 | 0.5 |
| 3.0 | 3.5 | 5.1 | 3.9 | 2.3 | 5.5 |
| 4.0 | 3.4 | 5.6 | 5.2 | 2.5 | 6.2 |
| 5.0 | 2.8 | 6.8 | 6.8 | 3.4 | 7.0 |
| 6.0 | 2.2 | 5.2 | 3.2 | 4.2 | 4.6 |
| 7.0 | 1.9 | 0.7 | 0.7 | 0.5 | 2.1 |
| 8.0 | 0.0 | 0.3 | 0.3 | 0.3 | 0.3 |

*Spontaneous $I_2$ production from $I^-$ under experimental conditions without added enzyme.
**Under the experimental conditions, the maximum theoretical production of molecular iodine is 11.2 mg (reactions are $H_2O_2$ limiting). Total iodine produced at a given pH is the sum of non-enzymatic plus enzymatic conversations.

EXAMPLE 2

The continuous production of iodine with chloroperoxidase is shown in this example. Chloroperoxidase is bound (immobilized) to calcium phosphate hydroxide (hydroxyapatite) and packed in a glass column (1.2 cm diameter by 10 cm height). The immobilized enzyme is prepared as follows:

15 ml of chloroperoxidase solution (prepared according to the protocol described in Example 1) is diluted to 100 ml with 1 mM potassium phosphate buffer pH 5.0, and loaded onto the glass column containing 15 ml of hydroxyapatite. The column is then washed overnight with 500 ml of 10 mM potassium phosphate buffer pH 5.0 at 5° C. The activity of the column is measured as 2235 monochlorodimedon units.

A reaction mixture containing 100 ppm (0.6 mM) potassium iodide and 5 ppm (0.14 mM) hydrogen peroxide in 0.1 M potassium phosphate buffer pH 3.0 is passed through the column at a flow rate of 2 ml/minute. The column eluant is collected in fractions. These fractions are then extracted with chloroform and the violet coloration in the chloroform layer is measured at 510 nm.

The following results are obtained:

| FRACTION | [$I_2$] |
|---|---|
| COLUMN IN | 2 μg/ml |
| COLUMN OUT | |
| 1st 100 ml | 24 μg/ml |
| 2nd 100 ml | 18 μg/ml |
| 3rd 100 ml | 16 μg/ml |

Under the experimental conditions, the maximum theoretical production of iodine would be 37 μg/ml, since the reactions are run under hydrogen peroxide limiting conditions. Over 50% of the theoretical yield is obtained.

The molecular iodine can be recovered from the column eluant by standard techniques known to those skilled in this art.

EXAMPLE 3

The continuous production of iodine with seaweed peroxidase immobilized on hydroxyapatite is shown in this example.

4 ml of Coralina sp. peroxidase supernatant (prepared according to the protocol in Example 1) is immobilized according to the procedure in Example 2, except the buffer is pH 6.0 instead of 3.0.

The reaction is run according to the procedure in Example 2, except the buffer is at pH 6.0.

The following results are obtained:

| FRACTION | [$I_2$] |
|---|---|
| COLUMN IN | 1 μg/ml |
| COLUMN OUT | |
| 1st 100 ml | 28 μg/ml |
| 2nd 100 ml | 29 μg/ml |
| 3rd 100 ml | 27 μg/ml |
| 4th 100 ml | 30 μg/ml |
| 5th 100 ml | 30 μg/ml |
| 6th 100 ml | 31 μg/ml |
| 7th 100 ml | 30 μg/ml |

Over 80% of the theoretical yield was obtained.

The molecular iodine can be recovered from the column eluant by standard techniques known to those skilled in this art.

EXAMPLE 4

The continuous production of iodine with seaweed peroxidase immobilized on glass beads is shown in this example.

The immobilized seaweed peroxidase is prepared as follows:

Glass beads (obtained from Sigma Chemical Company, PG-700-200) are activated by suspending 1 g of glass beads in 18 ml of deionized water. 2 ml of 10% v/v δ-aminopropyltriethoxyl silane are added and the pH of the mixture is adjusted to 3–5 with 6 N HCl. The mixture is shaken at 75° C. for 2 hours. The glass beads are then vacuum dried overnight at 80° C. 3.2 ml of purified Coralina sp. enzyme, prepared as in Example 1, and 50 mg of water soluble carbodiimide are added to the glass beads. The pH is adjusted to 4.5, and the mixture is then shaken at 4° C. overnight. The product—enzyme coated beads—is washed with water. The activity is measured as 2 monochlorodimedon units/g. of beads.

Using 1 g of the seaweed peroxidase coated glass beads, the reaction is run according to the procedure in Example 3.

The following results are obtained:

| FRACTION | [I$_2$] |
| --- | --- |
| COLUMN IN | 1 μg/ml |
| COLUMN OUT | |
| 1st 100 ml | 20 μg/ml |
| 2nd 100 ml | 21 μg/ml |
| 3rd 100 ml | 19 μg/ml |
| 4th 100 ml | 23 μg/ml |

Over 50% of the theoretical yield is obtained.

The molecular iodine can be recovered from the column eluant by standard techniques known to those in this art.

EXAMPLE 5

The continuous production of iodine with lactoperoxidase is shown in this example.

0.5 ml of lactoperoxidase (bovine milk) bound to Sepharose (purchased from P-L Biochemicals, Inc; Catalogue #0723; 10 units triiodide activity total) is run under the same column reaction conditions as in Example 3.

The following results are obtained:

| FRACTION | [I$_2$] |
| --- | --- |
| COLUMN IN | 1 μg/ml |
| COLUMN OUT | |
| 1st 100 ml | 35 μg/ml |
| 2nd 100 ml | 36 μg/ml |
| 3rd 100 ml | 35 μg/ml |

Over 90% of the theoretical yield is obtained.

The molecular iodine can be recovered from the column eluant by standard techniques known to those skilled in this art.

EXAMPLE 6

The continuous production of iodine with chloroperoxidase and with in situ generation of hydrogen peroxide is shown in this example.

Chloroperoxidase and glucose oxidase are bound to hydroxyapatite and packed in a glass column (1.2 cm diameter by 10 cm height). The immobilized enzymes are prepared as follows:

10 ml of chloroperoxidase solution (prepared according to the protocol in Example 1) and 5 ml of glucose oxidase, (purchased from Sigma Chemical Company; Catalog #G-6500), are diluted to 100 ml with 1 mM potassium phosphate buffer pH 5.0, and loaded onto the glass column containing 15 ml of hydroxyapatite. The column is then washed overnight with 500 ml of 10 mM potassium phosphate buffer pH 5.0 at 5° C. The activity of the column is measured as 1490 monochlorodimedon units of chloroperoxidase and 7400 o-dianisidine units of glucose oxidase.

A reaction mixture containing 100 ppm (0.6 mM) potassium iodide and 1800 ppm (10 mM) β-D-glucose in 0.1 M potassium phosphate buffer pH 4.4 is passed through the column at a flow rate of 2 ml/min. The column eluant is collected in fractions. These fractions are then extracted with chloroform and the violet coloration in the chloroform layer was measured at 510 nm.

The following results are obtained:

| FRACTION | [I$_2$] |
| --- | --- |
| COLUMN IN | 0 μg/ml |
| COLUMN OUT | |
| 1st 100 ml | 49.6 μg/ml |
| 2nd 100 ml | 44.8 μg/ml |
| 3rd 100 ml | 48.8 μg/ml |

Over 50% of the iodide is converted to iodine. In this experiment the production of iodine is limited by the in situ production of hydrogen peroxide.

The molecular iodine can be recovered from the column eluant by standard techniques known to those skilled in the art.

EXAMPLE 7

The continuous production of iodine with seaweed peroxidase and with in situ generation of hydrogen peroxide is shown in this example.

3 ml of Coralina sp. preparation (prepared according to protocol in Example 1) and 5 ml of glucose oxidase, (purchased from Sigma Chemical Company; Catalog #G-6500) are immobilized on hydroxyapatite as in Example 6, except the buffer is pH 5.0 instead of 4.4.

The activity of the column is measured as 51 monochlorodimedon units of seaweed peroxidase and 7400 0-dianisidine units of glucose oxidase.

The reaction is run according to the protocol in Example 6, except the buffer is at pH 5.0.

The following results are obtained:

| FRACTION | [I$_2$] |
| --- | --- |
| COLUMN IN | 0 μg/ml |
| COLUMN OUT | |
| 1st 100 ml | 16.0 μg/ml |
| 2nd 100 ml | 24.4 μg/ml |
| 3rd 100 ml | 16.0 μg/ml |

Over 50% of the iodide is converted to iodine. In this experiment, the production of iodine is limited by the in situ production of hydrogen peroxide.

The molecular iodine can be recovered from the column eluant by standard techniques known to those skilled in this art.

EXAMPLE 8

The simultaneous production/recovery of iodine in a repetitive batch, biphasic system is shown in this example.

To a 50 ml Erlenmeyer flask are added 10 ml of organic solvent (chloroform, carbon tetrachloride, xylene or carbon disulfide); 1 ml of lactoperoxidase bound to Sepharose (purchased from P-L Biochemicals, Inc.; Catalog #0723; activity listed at 20 triiodide units); 1 ml of 0.1 M potassium phosphate buffer pH 5.0; and a stir bar.

By use of a buret, a reaction mixture, which consists of 100 ppm (0.6 mM) potassium iodide and 7 ppm (0.2 mM) hydrogen peroxide in 0.1 M potassium phosphate buffer pH 5.0, is added to the flask at a rate of 5 ml/minute. The flask contents are stirred by use of a magnetic stirrer. After 30 ml of reaction mixture is added, the addition is stopped. The organic solvent layer is separated from the aqueous layer. This organic solvent layer is measured at 510 nm to determine the molecular iodine level produced.

The aqueous layer is centrifuged at 1000 rpm to pellet the immobilized enzyme. The pellet is returned to the 50 ml Erlenmeyer flask, fresh organic solvent is added (10 ml) and another portion of reaction mixture is slowly added (30 ml total addition volume at a 5 ml/min rate). The two layers are separated, processed and the reaction procedure repeated several more times.

The following results are obtained:

| SAMPLE | IODINE PRODUCED, mg | | | |
|---|---|---|---|---|
| | CHCl$_3$ | CCl$_4$ | Xylene | CS$_2$ |
| Control Batch* REACTION | 0 | 0 | 0 | 0 |
| 1st Batch | 1.2 | 1.5 | 1.5 | 1.5 |
| 2nd Batch | 1.4 | 1.5 | 1.5 | 1.4 |
| 3rd Batch | 1.5 | 1.5 | | |
| 4th Batch | 1.4 | | | |
| 5th Batch | 1.5 | | | |
| 6th Batch | 1.5 | | | |

*no enzyme added.

Under experimental conditions, the maximum theoretical production of iodine would be 1.5 mg since the reactions were run under hydrogen peroxide limiting conditions. Up to 100% of the theoretical yield is obtained.

The molecular iodine can be recovered from the organic solvents by standard techniques known to those skilled in this art.

EXAMPLE 9

The simultaneous production/recovery of iodine from iodide solutions high in other halides is shown in this example.

The procedure of Example 8 is followed with the following modifications:

(a) carbon tetrachloride is the organic solvent.

(b) seawater bittern which contains 140 mg/ml chloride ion and 1 mg/ml bromide ion is used. Iodide ion is not present at a detectable level. To this bittern, potassium iodide (100 ppm, 0.6 mM; final) is added.

The following results are obtained:

| SAMPLE | IODINE PRODUCED, mg |
|---|---|
| Control Batch* REACTION | 0 |
| 1st Batch | 1.5 |
| 2nd Batch | 1.5 |

*no enzyme added.

Under experimental conditions, the maximum theoretical production of iodine would be 1.5 mg, since the reactions were run under hydrogen peroxide limiting conditions. 100% of the theoretical yield is obtained.

The molecular iodine can be recovered from the organic solvent by standard techniques known to those skilled in the art.

Various modifications of the invention will become apparent to those skilled in the art from the foregoing description. Such modifications are intended to fall within the scope of the appended claims.

What is claimed is:

1. A method for producing iodine, comprising, providing, in the absence of iodine acceptor substrates, a reaction mixture of water, a halogenating enzyme, an oxidizing agent, a water-immiscible organic solvent, and a source of ionic iodide, buffering said reaction mixture to maintain it at a pH of between about 2 to 8, and recovering the molecular iodine continuously in said organic solvent as it is formed by said reaction mixture.

2. A method according to claim 1 wherein the source of ionic iodide is brine.

3. A method according to claim 1 wherein the source of ionic iodide is bittern.

4. A method according to claim 1 wherein said halogenating enzyme is a peroxidase derived from a member of the group consisting of the microorganism *Caldariomyces fumago*, seaweed, milk, thyroid, leukocytes, and horseradish.

5. A method according to claim 1 wherein said oxidizing agent is hydrogen peroxide.

6. A method according to claim 5 wherein said hydrogen peroxide is generated in situ.

7. A method according to claim 1 wherein said halogenating enzyme is immobilized.

8. A method according to claim 1 wherein said halogenating enzyme is immobilized, and wherein said oxidizing agent is generated in situ enzymatically using a further enzyme which is also immobilized.

* * * * *